(12) United States Patent
Moore et al.

(10) Patent No.: US 7,189,331 B2
(45) Date of Patent: Mar. 13, 2007

(54) CENTRIFUGE ADAPTER

(75) Inventors: Patrick Q. Moore, Gilroy, CA (US); Christopher L. Stewart, Santa Clara, CA (US)

(73) Assignee: Beckman Coulter, Inc., Fullerton, CA (US)

(*) Notice: Subject to any disclaimer, the term of this patent is extended or adjusted under 35 U.S.C. 154(b) by 101 days.

(21) Appl. No.: 11/077,746

(22) Filed: Mar. 10, 2005

(65) Prior Publication Data

US 2005/0194325 A1 Sep. 8, 2005

Related U.S. Application Data

(63) Continuation of application No. 10/413,881, filed on Apr. 15, 2003.

(51) Int. Cl.
*B04B 5/02* (2006.01)
*B04B 15/00* (2006.01)

(52) U.S. Cl. .................. 210/781; 210/782; 422/72; 422/102; 422/104; 494/16; 494/20; 494/37; 494/45; 494/85

(58) Field of Classification Search ................ 210/781, 210/782; 422/72, 102, 104; 494/16, 20, 494/37, 45, 85
See application file for complete search history.

(56) References Cited

U.S. PATENT DOCUMENTS

| 3,190,546 A | 6/1965 | Raccuglia et al. |
| 3,830,425 A | 8/1974 | Stallman |
| 4,413,773 A | 11/1983 | Rohde et al. ................. 494/37 |
| 4,531,652 A * | 7/1985 | Hara ........................... 494/20 |
| 4,692,137 A | 9/1987 | Anthony ...................... 494/85 |
| 4,832,678 A | 5/1989 | Sheeran ....................... 494/16 |
| 5,158,749 A | 10/1992 | Eberle ........................ 422/102 |
| 5,236,409 A | 8/1993 | Romanauskas .............. 494/85 |
| 5,295,943 A | 3/1994 | Romanauskas .............. 494/16 |
| 5,310,527 A | 5/1994 | Romanauskas et al. ..... 422/102 |
| 5,382,220 A | 1/1995 | Romanauskas et al. ....... 494/85 |
| 5,399,144 A | 3/1995 | Romanauskas et al. ....... 494/85 |
| 5,422,018 A | 6/1995 | Saunders et al. ........... 210/787 |
| 5,562,583 A | 10/1996 | Christensen ................. 494/16 |
| 5,626,749 A | 5/1997 | Lambert et al. ......... 210/257.1 |
| 5,935,052 A | 8/1999 | Hall et al. .................... 494/10 |
| 6,387,030 B1 | 5/2002 | Moore et al. ................. 494/20 |

FOREIGN PATENT DOCUMENTS

FR 2058578 5/1971

OTHER PUBLICATIONS

PTO 2005-3894-Translation of French Patent Document No.-FR 2,058,578, published May 28, 1971.*
Hartman, M., "Das Zentrifugieren von Zellkulturen in Flaschen", GIT Spez., Sep. 2000:20 (1) . [with translation].

* cited by examiner

*Primary Examiner*—David A. Reifsnyder
(74) *Attorney, Agent, or Firm*—Schneck & Schneck; Thomas Schneck; David M. Schneck (57) ABSTRACT

An adapter for use with a centrifuge. Features of the adapter allow for less friction during extraction of the adapter and separation efficiency by preventing disturbances to the separated materials. In addition, the adapter includes features that support the walls of a sample container and prevent force from damaging the sample container during a centrifuge separation procedure.

12 Claims, 9 Drawing Sheets

CENTRIFUGE ADAPTER

CROSS-REFERENCE TO RELATED APPLICATION

This is a continuation of U.S. patent application Ser. No. 10/413,881 filed Apr. 15, 2003, now allowed.

TECHNICAL FIELD

The present invention pertains to a device for use with centrifuges and specifically to adaptive media, which holds sample containers to be subjected to centrifugal force.

BACKGROUND OF THE INVENTION

Centrifuge instruments are in common use in research and industrial applications to subject samples to centrifugal force, thereby separating sample components by sedimentation properties. The liquid sample is placed in a container and placed in or attached to a centrifuge rotor. The centrifuge rotor is then rotated by the centrifuge instrument to effect a separation of the components of the liquid sample.

Containers of various sizes and shapes may need to be used in a separation procedure. A rotor for a centrifuge is commonly constructed to hold sample containers having a different diameter or shape than the containers that are actually used to hold a sample. To allow use of a variety of containers, adapters are commonly used with the centrifuge rotor. Such adapters are commonly constructed of a polymeric material but not limited to and constructed as a single piece having a shape which allows retention of one or more containers in which a sample may be placed. The adapter is inserted into a device mounted on or in a centrifuge rotor. The labware holding the sample is inserted in the adapter.

For example, U.S. Pat. No. 6,387,030 discloses an adapter for centrifuge containers having an open top, an interior surface and an exterior surface. The exterior surface of the adapter conforms to the bottom of a cavity in a centrifuge rotor device, such as a swinging bucket held by a rotor. The interior surface of the sample container has an internal sidewall and a bottom having a well to hold a pellet of denser material which has migrated under a centrifugal force. The pellet well extends radially outward from the center of rotation when the adapter is used with a swinging bucket rotor. This configuration allows the pellet to be confined to a localized area resulting in allowing a more compact pellet which remains intact as the adapter is extracted from the centrifuge rotor.

In designing of centrifuge adapters, one issue of concern is preventing agitation of the sample following a centrifuge procedure. Agitation of the sample may cause particulate or denser sample component to become mixed with less dense liquids. For example, U.S. Pat. No. 4,832,678 discloses a tube adapter for centrifuge rotor which includes a plurality of recessed grooves at the top of the adapter to allow engagement of a prong of a removal tool to extract the adapter from the recess of the rotor. Such a system allows an adapter to be extracted even if the adapter sticks somewhat to the recess of a body of a centrifuge rotor. However the disadvantage of using such an extraction system is substantial resuspension of the separated sample material.

The body of a centrifuge rotor is most commonly made of a metal alloy. The adapters are often made of an elastomeric or polymeric material. Such resilient plastic may stick against the surface of the rotor requiring some force in extraction. This is compounded by the centrifugal force of rotation which exerts pressure on the adapter into the rotor body. In addition to spilled or condensed liquids, close tolerances may seal the adapter into a receiving receptacle, creating a vacuum which is difficult to break.

To allow better integrity of a sample following centrifuge rotation, a number of split body tube adapters have been devised. For example, U.S. Pat. No. 4,692,137 discloses a split body adapter which may be hinged at a seam. When the two sections of the adapter are brought into opposing alignment, a recess within the adapter body forms a cavity for receiving a centrifuge tube. These two recessed sections may be substantially identical. During the application of centrifugal force, the behavior of the adapter and the sample container may differ since the adapter is usually made of a different material than the sample container. In many cases the tube deforms into the interior cavity of the adapter. Following the deceleration of the centrifuge rotor, the sample container must be removed from the adapter for subsequent processing and analysis of the sample within the sample container. The described adapter allows the sample container to be removed with reduced force. This allows integrity of the separated sample to be maintained. U.S. Pat. Nos. 5,295,943, 5,399,144, and 5,382,220 disclose a family of related adapters having a pair of hinged adapter body parts which are closed over all or part of a sample container. Another adapter configuration is disclosed in U.S. Pat. No. 5,236,409 in which a sample container is inserted into a centrally cylindrical recess in a tube adapter. A clamp on the bottom of the adapter extends over a second piece of a top inserted over the centrifuge container. This forms a single adapter unit which may subsequently be subjected to centrifugal forces. U.S. Pat. No. 5,935,052 discloses an adapter for fixed angle centrifuge rotor including a pair of adapter sections, which are pressed together to form a unitary structure surrounding a sample container.

While the above adapters have provided a number of alternatives for use with centrifuge rotors and subjecting sample containers to centrifugal forces, some problems remain. For a number of sample containers, it remains difficult to extract sample containers from the adapter, and the adapter from a centrifuge rotor, and such extraction may agitate the sample, thus reducing the separation efficiency.

Additional concerns exist for centrifuge separation using more fragile sample containers that are in common use. One example of such containers are cell culture flasks (also referred to as tissue culture flasks). Cell culture flasks are commonly made of polystyrene or some other similar material. Cell culture flasks generally have a rectangular cross section. This allows efficient stacking of the flasks on incubators for incubation of cell cultures. Such flasks generally are comprised of two or more parts attached at a seam by ultrasonic welding or similar attachment means. Large numbers of such flasks are presently used for a number of different cell culture processes, including culture of adherent cells and suspension cell culture. The current use of such cell culture flasks for the growth of cell cultures does not subject the flask to vacuum or any pressures beyond ambient pressure. (1 g=1 times the force of gravity)

It would be advantageous to be able to harvest cells within cell culture flasks. Common protocols currently require that cells grown in tissue culture flasks be subsequently transferred to an alternative container, such a conical tube, prior to subjecting cells to harvesting by centrifugal force. The cells may then be separated from the surrounding media which would be decanted or aspirated to remove this liquid. The cells may then be resuspended in a new media and subsequently regrown. These procedures have a number of drawbacks. First, a large number of sample containers must be used in each transfer step with attendant cost of labware and disposal of used labware. Second, an experimentalist's time is required for each transfer step. Third, each transfer step from a flask to a centrifuge container (such as a conical tube) has the risk of contaminating cell lines. Such cell lines may be rare and expensive and represent many hours of preparation effort. Finally, the transfer of cells from the cell culture flask may result in loss of cells and possibly degradation of cell lines. Given the time and expense of preparation of such cell lines, minimization of transfer steps would be beneficial.

It is an object of the invention to provide a centrifuge container adapter which facilitates removal of the adapter from the rotor with minimal mixing of separated sample. It is a further object that such an adapter be lightweight. It is a further object of the invention to provide an adapter which is adaptable to use with cell culture flasks. Such an adapter would maintain of the integrity of these flasks while still allowing efficient separation.

SUMMARY OF THE INVENTION

The above objects have been achieved with an adapter to hold a sample container having features that allow for efficient separation. In various embodiments these features support the sample container, accommodate raised features on the outer surface of sample containers and allow a container to be spun and removed from an adapter with minimal disturbance of the separated sample material. In one embodiment a recessed portion of each adapter section are brought together into alignment by the hinge such that the recessed portions form a pocket which holds a centrifuge container. The sections are separated by a slit extending from the open top of the pocket to a location proximate to the bottom of the pocket. The walls of the pocket have ribs which run down the length of the wall of the pocket, providing support to a container wall inserted in the pocket.

The present adapter may include a number of features. A first such feature is ribbing on the exterior surface of the adapter that contacts the rotor device into which the adapter is inserted. Exterior ribbing will reduce friction during extraction of the adapter. A second feature is through holes extending through the adapter sections to reduce adapter mass and ease extraction of the adapter from a rotor device by breaking any vacuum between the rotor device and the adapter. A third feature is a vent hole that passes through the bottom of the sample container pocket to break any suction between the bottom of the adapter and a rotor device used with the present adapter. A fourth feature is a hinge groove to reduce the thickness of material at the hinge location, and to increase the durability of the hinge. A fifth feature is a slit that may include a cutout at the lowest portion of the slit, which also would add to the durability of the hinge. A sixth feature is an orientation indicia to indicate to a user the proper alignment of the sample container to the adapter and the adapter with the rotor device.

A seventh feature is the presence of one or more grooves in the interior of the pocket to prevent force load from concentrating on a ridge, seam, leg, or other protrusion from the exterior surface on the sample container. For cell culture flask adapters, the relatively delicate seam is fit into an adapter seam groove, such that the centrifugal force is distributed onto the walls of the flask. These walls are supported by the pocket ribs, thus preventing seam failure. The legs of the sample container and stacking ridges on the edges of the sides of the sample container also may be accommodated in a recess. The ribs extend to prevent the load from bearing onto the ridges or legs and instead allow the load to be distributed across the surface of the sides or bottom of the flask during centrifugal rotation. An eighth feature of the present invention is handles, which may be used to compress the sections of the adapter together to aid in extraction of the adapter from a centrifuge rotor.

The adapter may include more than one pocket, and may include more than two sections defining the pockets.

One aspect of the present invention is a method of using the present adapter. In one embodiment of this method for use with cell culture flasks, the adapter is inserted into the rotor device so that the separated sample material that forms a pellet during centrifugal rotation is distributed along a side of the flask which does not have a weld seam. This prevents a load from concentrating at the seam and endangering the seam. Orientation +/−15 degrees of alignment should be tolerated.

DETAILED DESCRIPTION OF THE INVENTION

Figure 1:
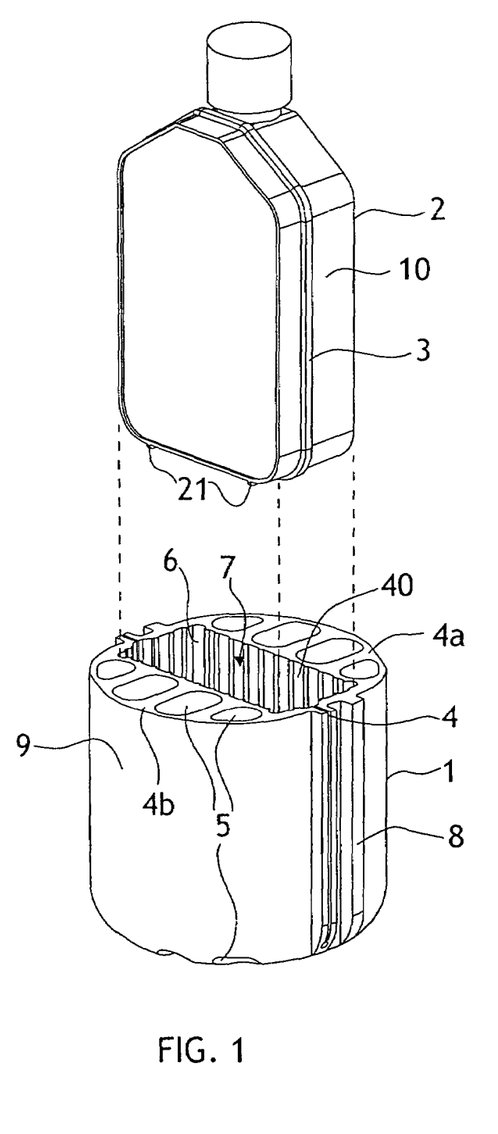
FIG. 1 is a perspective view of a cell culture flask and an adapter in accord of the present invention.

With reference to FIG. 1, a first embodiment of a tissue culture adapter 1 and an associated cell culture flask 2 to be held by adapter 1 is shown. The flask is shown in the proper insertion orientation such that the flask would be held securely by the adapter.

With respect to the tissue culture flask 2, such flasks are typically manufactured as two parts joined together at seam 3. Such parts are joined by ultrasonic welding or another bonding means. Ultrasonic welding may be preferred to the use of an adhesive to prevent outgassing problems. Such tissue culture flasks are generally designed to be used at ambient pressure (1 g applications). In a typical experiment, a tissue culture flask is partially filled with a growth media, seeded with cells and placed in a suitable environment. Such a controlled environment may be an incubator. On such an incubator, the flask is placed flat, allowing both efficient stacking of the flasks and providing a large surface area (one flat side of the flask) for cell growth. This orientation also provides a greater surface area of the media to exchange gases with the air above the growth media. The flask may have a vented cap to allow gas exchange. A hydrophobic liner in the cap retains liquid within the flask. Such incubators may be fully enclosed by a housing allowing control of the environment at which cells are grown.

Flasks are typically made of a clear polymeric material such as polystyrene or other similar polymer. The flasks are designed to allow visual inspection by a researcher of the contents of the flask contents. Large surfaces of the walls of the flasks are relatively thin and unsupported and the two halves of the flasks are secured by simple bonded joint. Such flasks are produced as a disposable product and are consumed by millions each year. These flasks were originally not designed to be subjected to centrifugal force. The present adapter allows 100 to 2,000 relative centrifugal force (g force) range to be applied to the flask to separate cells from growing media without compromising the structural integrity of the tissue culture flask.

The structure of the flask must be accommodated by any adapter. Seam 3, the location of the attachment of the two parts forming the flask, is a raised seam extending on two sides, top and bottom of the flask. In addition the flasks commonly have legs 21 to allow the flask to stand upright on a flat surface. These structures must be accommodated by any adapter.

Adapter 1 allows tissue culture flask to be easily inserted and removed from adapter 1. The adapter is comprised of a first adapter section 4A and a second adapter section 4B. Slits 4 extend from the top of the adapter to approximate to the bottom of the adapter. This allows adapter sections 4A, 4B to flex in opposing directions, providing an easier insertion and removal of an associated tissue culture flask into the interior pocket 7.

Extending through the body of adapter 1 are through holes 5. These through holes serve both to lighten the overall weight of adapter 1 and to help release any suction which might occur at the bottom of adapter 1 between the adapter and a swinging bucket type rotor. Through holes 5 also serve to reduce the buckling load placed on the flat face of the flask.

Flask 2 is received into pocket 7 of adapter 1. Pocket 7 has an interior surface 40 having a plurality of ribs 6 disposed throughout the interior of the pocket. These ribs extend from the opening of the adapter to the bottom floor of the adapter. When flask 2 is inserted into adapter 1, the ribs provide support to the sides of the flasks while at the same time preventing the relatively softer material from which the adapter is manufactured from adhering to the relatively harder material of which flask 2 is made. The ribs 6 also by design and shape contribute to supporting the large flat flask face while not significantly loading it. Also, the ribs assist with extraction of the adapter by making the adapter more compressible. In one embodiment, ribs 6 reduce the contact area between the adapter and the side walls of the container by 89%.

External support ribs 8 which provide additional side support to pocket 7 are located proximate to slit 4 on the exterior 9 of the adapter 1 on each of two sides of adapter 1. In addition, support ribs 8 reduce the overall weight of the adapter by providing a support structure for the adapter against the side of the bucket into which the adapter will be inserted. Ribs 8 also reduce loading on side 10 of tissue culture flask 2. The steps to reduce loading of the tissue culture flask 2 are important because flask 2 does not have structural support to withstand significant side loads at the location of seam 3 on tissue culture flask 2. Empirical testing has demonstrated that excessive side loading on side 10 and the flat face 13 at the location of seam 3 on the tissue culture flask 2 may cause failure of the tissue culture flask seam 3 even at relatively low centrifugal loads.

Figure 1A:
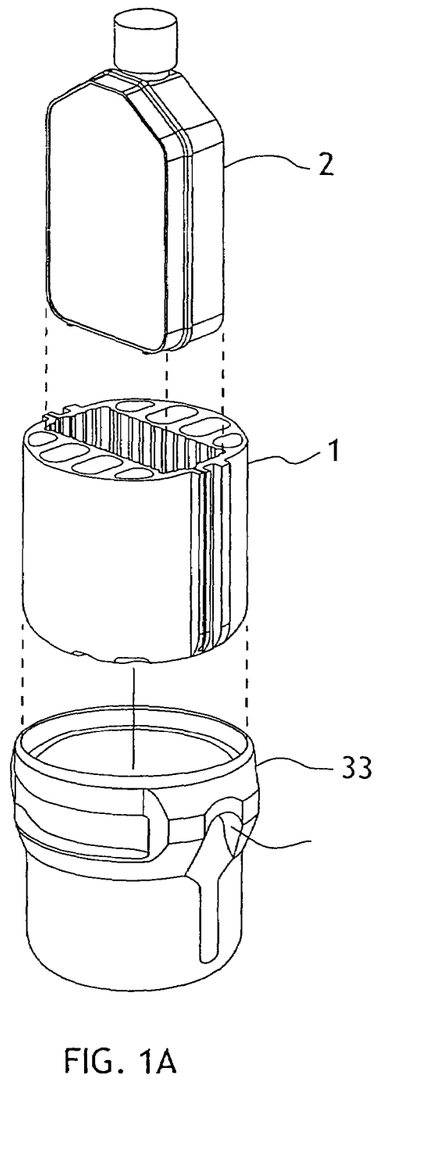
FIG. 1A is a perspective view of a cell culture flask, an adapter (as in FIG. 1) and a swinging bucket rotor.

With respect to FIG. 1A, it can be seen that flask 2 may be inserted into adapter 1 which is subsequently fit into rotor bucket 33. Rotor bucket 33 has pivot mounts 42 allowing this bucket to be mounted onto a centrifuge rotor. Upon rotation, the orientation of the bucket changes so that the bucket is on its side. This presents the bottom of the flask at the greatest radial distance from the center of the rotation. Sample components of greater density then migrate to the bottom of the flask inserted into adapter 1 held in bucket 33. This is explained in greater detail in relation to FIG. 10.

Figure 2:
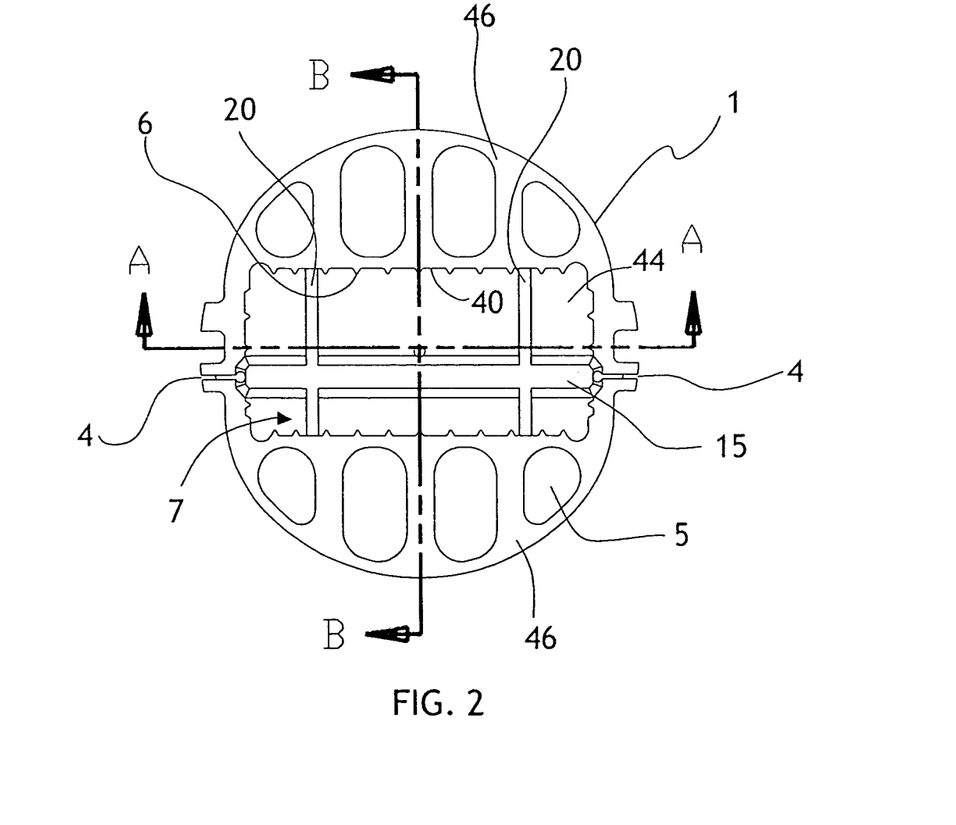
FIG. 2 is a top view of the adapter of FIG. 1.

The top view of adapter 1 shown in FIG. 2 illustrates the details of the construction of the adapter device. Through holes 5 extend from the top surface 46 of the adapter through the bottom of adapter 1. Pocket 7 holds the cell culture flask. At the bottom of pocket 7, grooves 20 on bottom surface 44 allow the support legs of the flask (shown as element 21 on flask 2 in FIG. 1) to be accommodated. In this embodiment the bottom contact between adapter and container bottom is reduced to 81% of the bottom surface. Ribs on bottom surface 44 (ribs not shown) may further reduce the contact area while still providing adequate support for the container bottom. Also on bottom surface 44 at the bottom of pocket 7 is seam groove 15 extending between the sides of the adapter. This seam groove allows the seam of a tissue culture flask to be fit into the adapter. Positioning of the seam groove 15 and the side slits 4 of adapter 1 may be changed depending on the construction of the tissue culture flask being used with the adapter. The placement of the seam on various different flasks manufactured by different makers may vary. This flask seam may be on edge of one flat face of the flask, or may be between the sides of the flask. In addition, the locations of slits 4 are preferably aligned with the location of seam groove 15. Thus the two halves (sections) of the adapter created by slits 4 may be unequal, as is shown in FIG. 2. In addition, slits 4 may not always be aligned with seam groove 15.

Ribs 6 extend from proximate to the top surface 46 to proximate to the bottom surface 44, extending down interior surface 40 in pocket 7. These ribs extend down all four sides of pocket 7. During rotation, the adapter ribs 6 support but not crush the sides of a flask inserted in the adapter.

Figure 3:
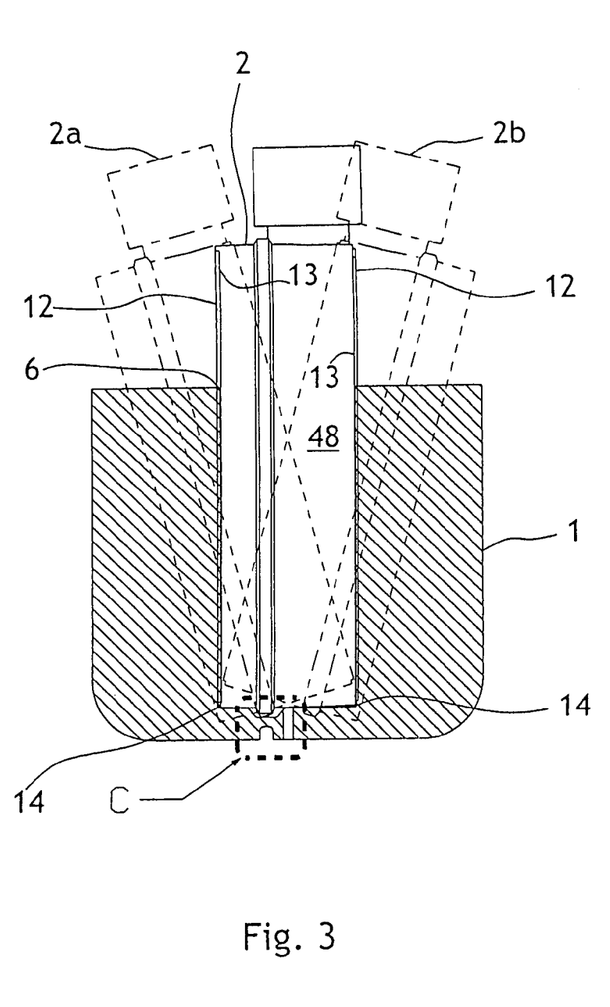
FIG. 3 is a side cross sectional view of the adapter of FIG. 2, taken along lines B—B, and shown with a flask inserted into the adapter.

The section lines B—B shown in FIG. 2 indicates the cross section shown in FIG. 3. This view shows a cell culture flask 2 inserted into adapter 1. This view illustrates an edge side 48 of tissue culture flask 2. Commonly, tissue culture flasks will have a peripheral ridge 12 to allow stacked flasks on an incubator to be interlocked together. These elevated ridges extend along the sides, top and bottom of the tissue culture flasks along edges on the front and back side of the tissue culture flask. The support ribs 6 must extend below the plane created by the tissue flask ridges 12 in order to support the flat faces of the sides of the tissue culture flasks. In this design, the tissue culture flask ridges 12 extend to the face of the side of the adapter as indicated at locations 14.

If the adapter did not have side slots which divide the internal pocket of the adapter into sections, the tissue culture flask would be removed by grasping the top of the flask and extracting the flask upward. During this upward dragging the external ridges 12 would be rubbed against the material of the inner pocket. Given the fact that the tissue culture flask is made of a rigid polymeric material such as polystyrene and that the adapter is made of a softer polymer such as polyurethane, the resulting drag would cause agitation of the tissue culture flask and risk resuspension of the pelleted cells or other separated material. Such agitation of the separated sample is not desirable given that it reduces the separation efficiency and yield of separated material. The present design overcomes this disadvantage by allowing the adapter to partially flex open for removal of the flask.

Figure 3A:
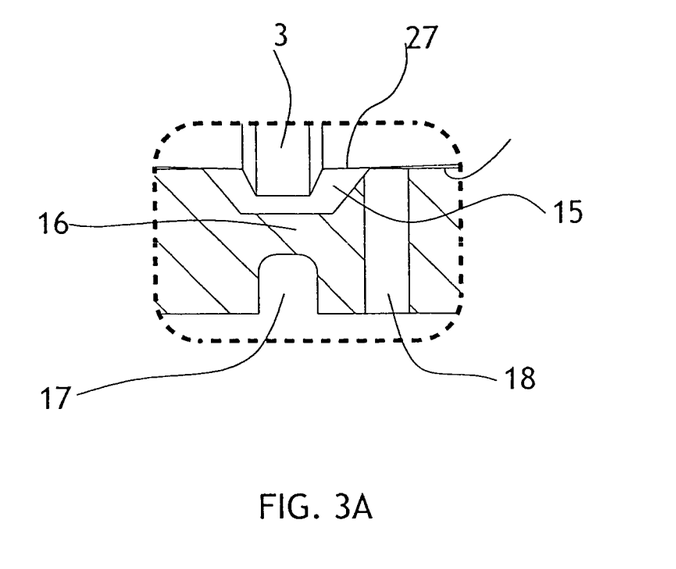
FIG. 3A is a detail of the adapter hinge shown in FIG. 3.

A dotted circle C of FIG. 3 is illustrated in FIG. 3A. This illustrates the hinge section of the adapter. Seam groove 15 eliminates the concentration of the centrifugal force on the relatively weak seam 3 of the tissue culture flasks while locating bottom surface 27 of the tissue culture flask onto bottom surface 44 of the adapter pocket. A hinge 16 is formed along the bottom of the adapter offset by flask seam groove 15 and opposing bottom notch 17. Notch 17 reduces the thickness of hinge 16. This increases the life of the hinge. In addition, the use of notch 17 also limits the angular degree to which hinge 16 may open when the halves of the adapter are moved in opposite directions. An interior pocket vent hole 18 allows any suction created between the rotor device (e.g. swinging bucket) and the tissue culture flask adapter to be broken during extraction of the tissue culture flask from the adapter. This may be particularly important if liquid is present in the rotor device, creating a seal which would be broken by hole 18. To aid in removal of the adapter, talc or other similar powder may be dusted onto the adapter.

Sectional lines A—A shown in FIG. 2 represent a cross-sectional view of the adapter illustrated in FIG. 4 again with the tissue culture flask 2 shown inserted in adapter 1. In this side view, the bottom surface 27 of tissue culture flask 2 rests on surface 44 at the bottom of the internal pocket of adapter 1. Legs 21 on tissue culture flask 2 are received into leg notches 20. This allows the adapter to support the bottom surface of the tissue culture flask, thus distributing the load to which the bottom of the tissue culture flask is subjected during centrifugal rotation.

Figure 4:
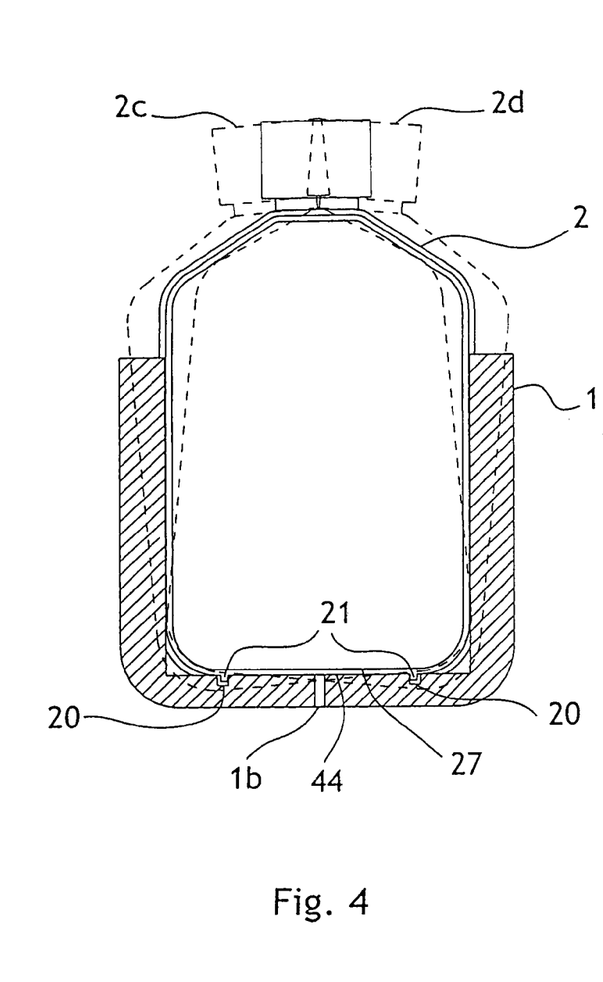
FIG. 4 is a cross sectional view along a first axis of the adapter of FIG. 2 taken along lines A—A, and shown with a flask inserted into the adapter.

In FIGS. 3 and 4 alternate embodiments of the adapters in which the sample containers are held at an angle are shown by lines 2a, 2b on FIGS. 3 and 2c, 2d on FIG. 4. The recess grooves, ribs and other features on the adapters would be repositioned to allow for support of the walls of the sample container and to provide an accommodating space for protruding elements on the container.

Figure 5:
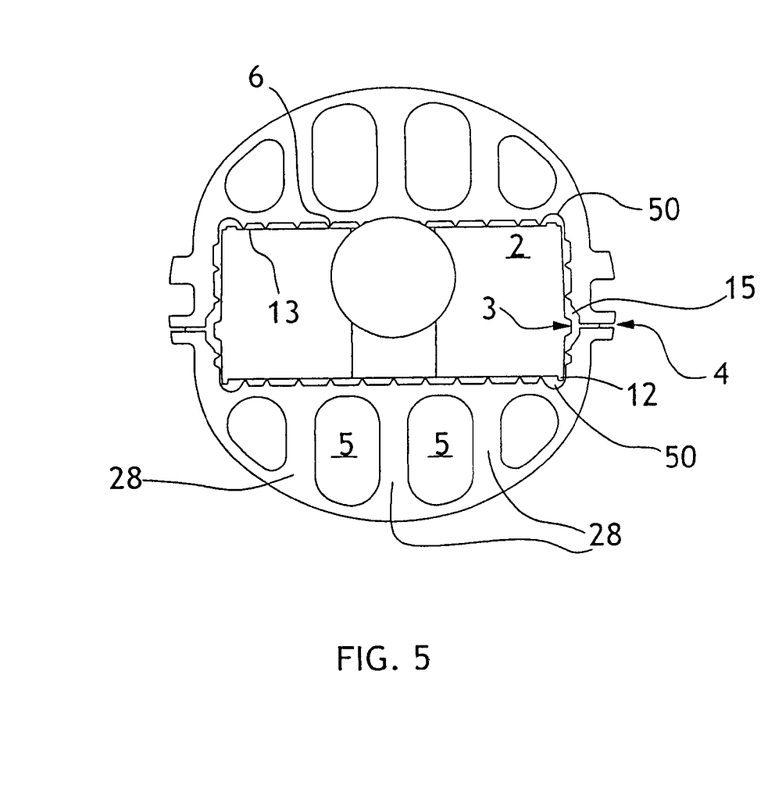
FIG. 5 is a top view of the adapter of FIG. 1 shown with the flask inserted.

FIG. 5 illustrates a top view of the adapter of the present invention with the adapter illustrated holding a tissue culture flask 2. This view illustrates the features of the present adapter which allow the force exerted during a centrifugal rotation of the flask to be evenly distributed about the sides of the flask. Flask seam 3 is positioned at seam groove 15 on the adapter. Thus the support forces are not concentrated at seam groove 3. Similarly the flask ridge 12 is contained in corner recess 50 such that ridge 12 does not bear the full load of the centrifugal forces. Side face 13 on the flask is supported by ribs 6 which extend down into the container pocket and are spaced along the interior wall of the pocket in which flask 2 is inserted. These ribs may be evenly spaced or may be grouped. The contact area of rib 6 is sufficient to support yet not overload flask sidewall 13 while still allowing ease of extraction and insertion of the flask from the adapter.

Adapter 1 includes through holes 5 which decreases the weight of the adapter. Between through holes 5 is ribbing 28 which provides support to the tissue culture flask sidewall 13 and also controls the buckling of wall 40. The ribbing 28 will not transfer the load to the flask wall while the adapter wall is undergoing distortion and loading during centrifugation.

The positioning of slot 4 and seam groove 15 are aligned and positioned on the adapter to receive seam 3 on cell culture flask. This groove both prevents the concentration of force at the relatively weak seam 3 and allows the tissue culture flask to be extracted without disturbing a separated sample. Locating slot 4 at seam 3 provides the optimal location for the seam at which the adapter is allowed to flex open, given that seam 3 represents the widest part of the tissue culture flask.

Figure 6:
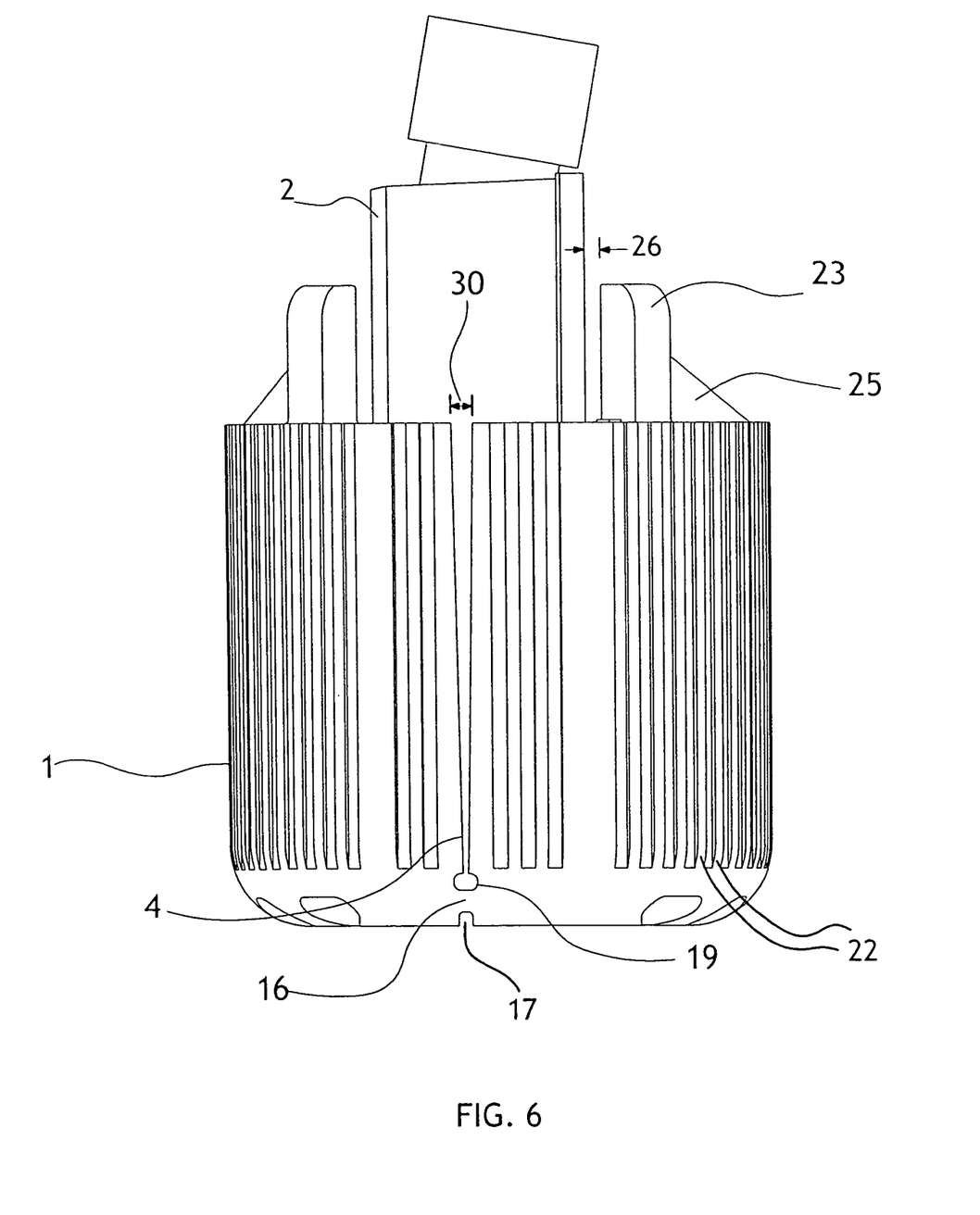
FIG. 6 is a side view of an alternative embodiment of the adapter, shown having handles to allow simplified extraction of the adapter from the rotor.

An alternative embodiment of the present invention is shown in FIG. 6. This embodiment includes features which make the adapter 1 both easier to remove from a centrifuge rotor swinging bucket and includes features which increase the life of the device.

Figure 7:
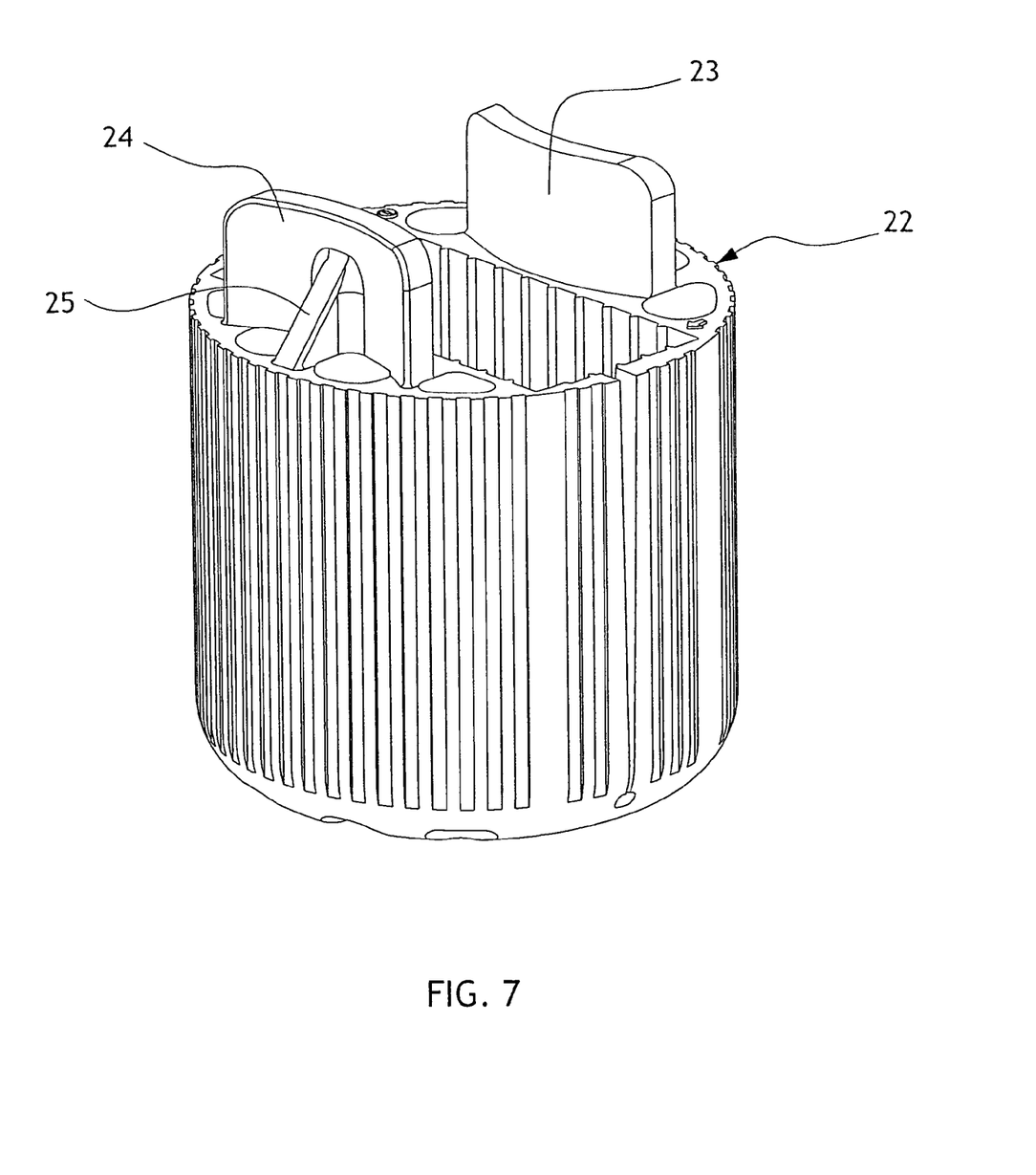
FIG. 7 is a perspective view of the adapter of FIG. 6.

External ribs 22 (also shown in FIG. 7) on adapter 1 reduce the surface contact between the adapter and a device attached to a centrifuge rotor into which the adapter is inserted (e.g. swinging bucket). Reducing the surface contact between the relatively harder material of the rotor device and the relatively softer material of the centrifuge adapter reduces the friction between these surfaces as the adapter is removed from the rotor device (e.g. swinging bucket). This is a first means by which agitation of the sample is minimized in this embodiment. A second means by which extraction of the adapter is aided is through the use of finger grips 23. The location of finger grip 23 is set back from the face of the flask 2 as indicated by width 26. This, in addition to rib 25, prevents the finger grips 23 from contacting the side walls of flask 2 during a centrifuge rotation procedure. This prevents additional forces from being exerted onto the sides of flask 2, thereby preventing damage to the flask. The distance of setback 26 from the face of flask 2 should be at least as great as the width 30 of slot 4. Support strip 25 is attached from the top of the adapter to the side of finger grip 23 constraining the movement of finger grip 23 in the direction of the flask during centrifugation, as illustrated in FIGS. 6 and 7. A textured surface 24 on finger grips 23 aids the user in extracting the adapter from a bucket into which the adapter has been inserted. Exerting force on finger grips 23 brings the opposing halves of the adapter closer together, narrowing the width of slit 4. This retracts adapter 1 from sides of the bucket into which the adapter has been inserted, reducing the drag during removal or insertion between the adapter and the bucket.

The finger grips 23 acts to bring the opposing sections of the adapter together. The sections pivot along the bottom of the adapter at hinge 16. Two features of the hinge 16 aid in extending the life of the hinge. The first is bottom groove 17 extending along the bottom of adapter 1. This groove (and the seam groove 15 seen in FIG. 3A) reduces the thickness of hinge 16 and additionally restricts the degree to which the halves of adapter 1 may be moves in opposite directions. In addition, cutout 19 at the base of slot 4 also prevents tearing of the hinge, thereby increasing the durability of the hinge during repeated extractions and insertions of associated sample containers.

Figure 8:
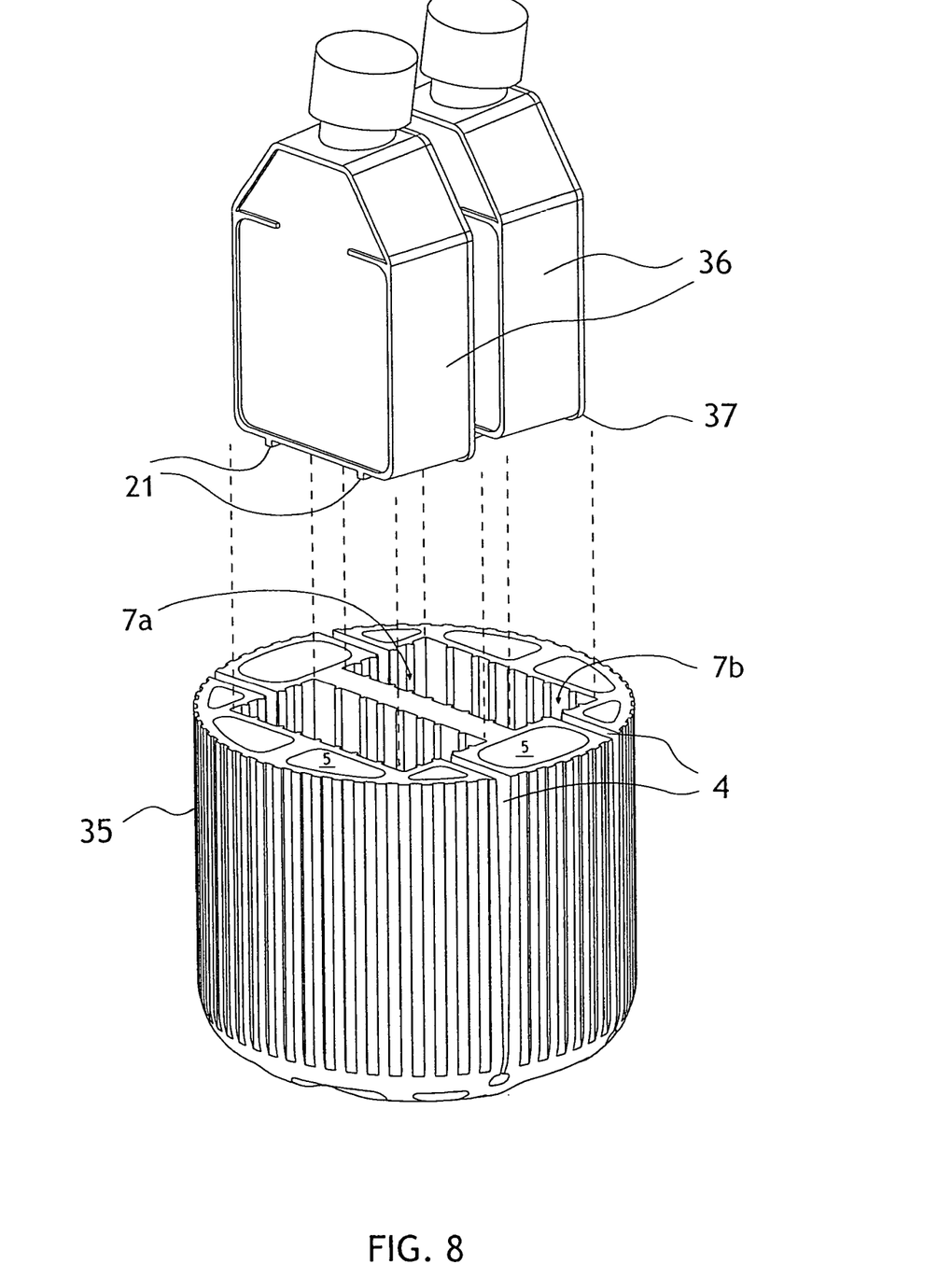
FIG. 8 is a perspective view of an alternative embodiment adapter designed to hold two flasks.
Figure 9:
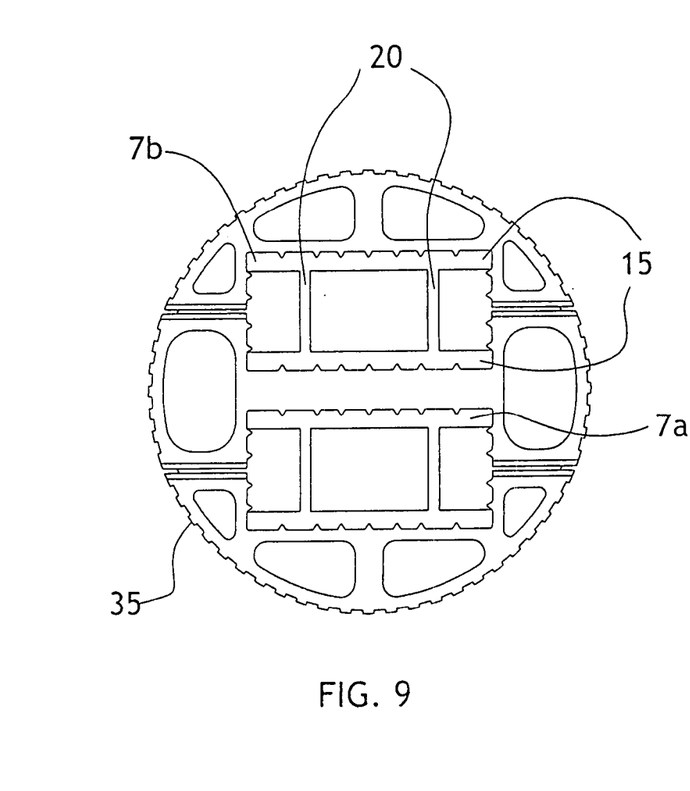
FIG. 9 is a top view of the adapter of FIG. 8.

FIGS. 8 and 9 show views of an alternative embodiment in which multiple flasks are held in a single adapter. In this embodiment, each pocket 7A, 7B has an associated slot allowing the adapter to separately flex. As in prior embodiments, this feature enables insertion or removal of each of the individual flasks. The number of pockets used may be based on the flask size selected by an experimentalist. The through holes 5 in this embodiment extend around the circumference of the adapter 35. Although not shown with finger grips, such grips may be added to aid in removal of adapter 35 from an associated centrifuge rotor device.

The vertical slots 4 again extend from the top of the adapter to proximate to the bottom of adapter. Slots on opposing sides of each of pockets 7A, 7B allow each pocket to individually flex open. The location of the slots in this illustrated embodiment is not aligned with the seams 37 of the flask. In addition, it may be advantageous in certain circumstances to include multiple slots for each pocket. Such slots could be positioned at the edges of the pockets at the location of seam groove 15.

As shown in FIG. 9, the bottoms of pockets 7A, 7B contain seam grooves 15 and grooves 20 to accommodate the seams of the flask and the leg struts 21 of the flasks (shown in FIG. 8). The use of multiple seam grooves at the bottom may allow a number of different flask models (of similar size) from different manufactures to be used with a single adapter. In addition, such seam grooves on both sides of the bottom of the pocket may allow the flask to be oriented in either direction.

Figure 10A:
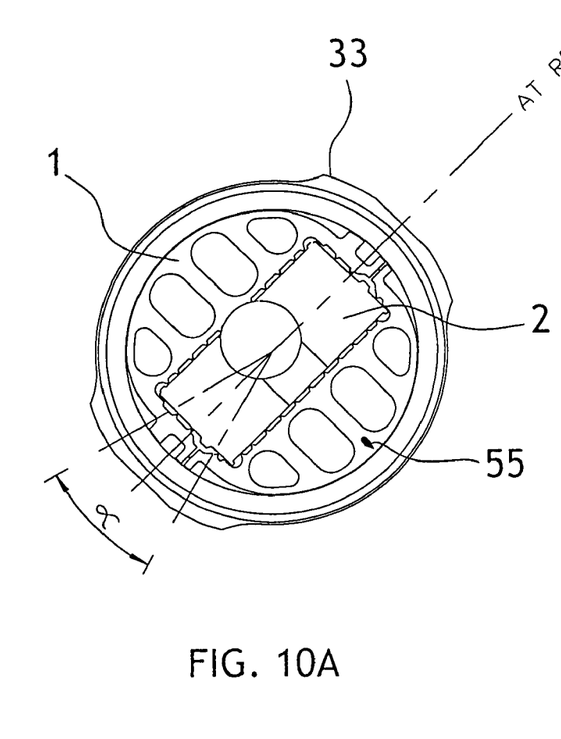
FIG. 10A is a top view of the adapter and flask inserted into a swinging bucket rotor, shown with indication of the center of rotation and shown prior to rotation of the rotor.
Figure 10B:
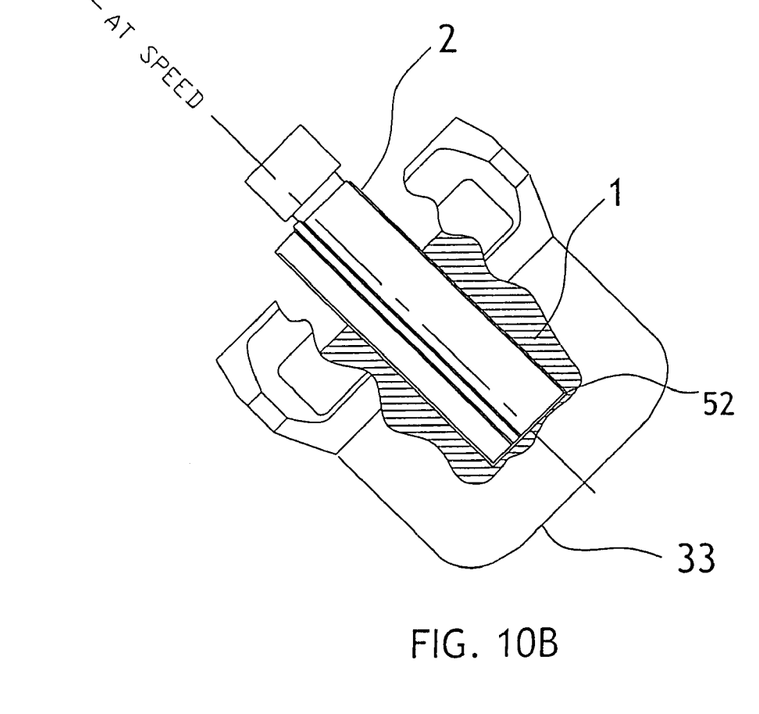
FIG. 10B is a cross section of the devices of FIG. 10A during rotation of the rotor.

FIGS. 10A and 10B show the top view of the flask adapter inserted in a swinging bucket centrifuge rotor at rest and during centrifugal rotation respectively. The orientation of the flask may be critical. It is preferable for the longer dimension of the flask to be oriented along the radius to the center of rotation when the flask is at rest. This orientation should be plus or minus 15 degrees as shown by angle α in FIG. 10A. During rotation of the flask, the radially greatest distance in the flask will be at the bottom corner of the flask along the longer side of the flask, indicated at 52 on FIG. 10B. Hydraulic loading during the sample separation (i.e. application of centrifugal force) will stress a seam if this force is concentrated on the seam. Thus it is preferred that the sample container be oriented such that hydraulic load is distributed along the longest dimension of the flask and preferably also away from the side of the flask on which the seam is located. This further attenuates risk of excessive force on the flask, particularly force concentrated along the edge of the flask having the seam, causing seam failure. Using this orientation allows maximization of the centrifugal forces that can be applied to the cell culture flask. The typical forces of 100–2,000 relative centrifugal force range used to separate cells from a growth media may be used with the present adapter in this orientation.

An indicia mark (55 in FIG. 10A) on the adapter may allow a user to quickly identify the proper orientation of the adapter in a bucket. For example, an arrow or other symbol on the adapter may be aligned with manufactures writing on the swinging bucket to allow for proper orientation of the adapter and flask in the bucket. In addition, orientation indices on the sample container or adapter could be used to indicate to a user proper insertion direction. This would be helpful to insure that the flask or other container is inserted into an adapter such that a seam ridge or other ridge on the sample container is fit into a recess or groove on the adapter.

Figure 11:
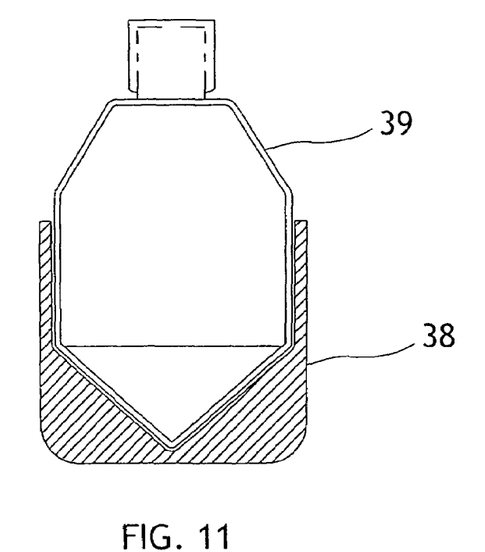
FIG. 11 is a front cross section of an alternate embodiment of the flask and adapter, where the flask includes a pellet well.
Figure 12:
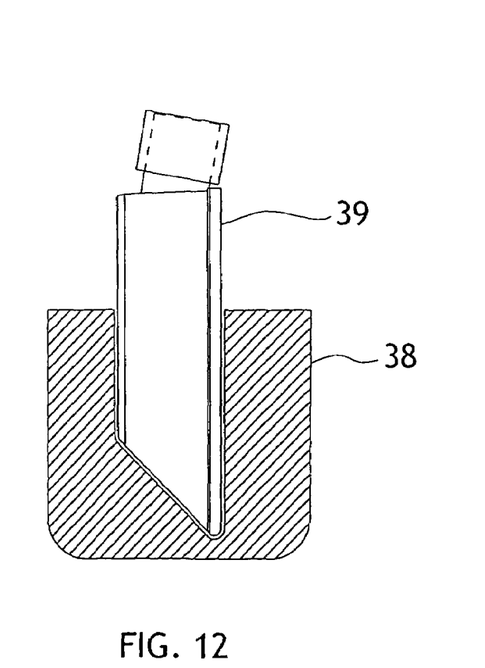
FIG. 12 is a side cross section of the flask and adapter of FIG. 11.

With respect to FIGS. 11 and 12, an alternative embodiment of an adapter and flask are shown. A number of tubes used in centrifuge separations include a conical bottom or other recessed or narrowed diameter space at the bottom of the tube to concentrate cells or other separated material in a localized area. It may be desirable to design a cell culture flask having a similar feature to allow simplified separations. As shown in FIGS. 11 and 12, the present adapter may accommodate such flasks. The elements of previous adapters, including through holes to reduce the weight of the adapter, internal and external ribbing, slots to simplify insertion and removal of the flask from the adapter and other features, could be included in this device. In addition, flask 39 could include stacking ridges and other features of tissue culture flasks described above.

The use of the adapters are illustrated in the following examples.

EXAMPLE 1

Starting Cell Lines from Frozen Stock

This process begins by releasing a cell line from a stock, such as frozen cells from a cell registry and depository. With the current protocol the cell line pellet is thawed and may be transferred to a conical tube containing media. This conical tube would then be subjected to centrifugal force (for example, 1,000 to 1,800 revolutions per minutes for 4 to 10 minutes at room temperature) to pellet the cells to the bottom of the tube. The supernatant would then be removed, for instance by pipette removal or decanting. A media would be added to the conical tube to resuspent the cells in the media. The resuspended cells would then be introduced to a tissue culture flask of a selected size such as the 75 cm$^2$ tissue culture flask, and the cells are grown in the media under the controlled environment of an incubator. Using the adapter of the present invention, the thawed cell line pellet may be transferred directly into a flask containing growth media. Subsequent centrifuge rotation to pellet the cells and removal of a supernatant would occur in the tissue culture flask, as would resuspension of the pellet itself into a media. Because a transfer step is eliminated, the risk of contamination is lowered and less experimentalist time is required.

EXAMPLE 2

Passing and Refeeding of Cells

The cell culture flask may be used to grow adherent cell culture or suspension cell cultures (such as from established cell lines or from primary cells (derived from blood, body fluids, tissues or organs). The cell line originate from a frozen cell stock or from primary cells needed to be resupplied with fresh nutrient media after a period of growth in the flask. In current protocols, the cells such as in the suspended cell culture or the detached cells from the adherent cell culture would be transferred to a conical tube or other similar labware and spun to pellet the cells. The supernatant would then be removed and additional culture media added to the tube. The cells would then be resuspended and transferred to cell culture flasks for continuing growth, or be divided into a number of flasks for additional growth. In using the present invention, such transfer of cells to conical tubes may no longer be necessary. Over the course of cell maintenance or expansion growth, the number of transfers between flasks and tubes eliminated by the use of the present adapter is quite significant. Each transfer bears the risk of contamination of the cell line. The present invention obviates the need for such transfers, reducing the risk of cell-line contamination. Given that such passing and refeeding steps may occur a number of times in the growth of cell cultures, the use of the present invention allows savings of time and cost at each of these repeated steps.

EXAMPLE 3

Harvesting of Cells

Finally, the harvesting of cells of analysis previously may require transferring of the cells and media from a flask, in which the cells were growing, to a conical tube. As before, the cells would be subjected to centrifugal force to pellet the cells. The media is removed, the cells are resuspended in the conical tube, adjusted to the appropriate concentration and subsequently transferred to be used for various end analysis. Alternatively, the concentrated cells may be transferred to vials or other storage containers for freezing and future reuse. The present adapter can eliminate the use of the conical tubes, instead allowing the centrifugation of cells to occur in the original tissue culture flask.

A person of ordinary skill in the art will appreciate that a number of alternatives are possible using the present device. For example, the illustrations detail the use of cell culture flasks for use with the present adapter. However, a number of different sample container, or microfluidic devices could be used with variations of the present adapter. Such an adapter would be able to support delicate sides of such a container or device or allow simplified insertion and extraction of the container or device from the adapter.

The adapter may be made of polyurethane or other similar material. A 60 durometer plastic may be used to provide a resilient material for the adapter. The adapter in the examples was manufactured as a single piece. This adapter may be produced by molding or extruding or other manufacturing means. However, the present invention includes adapters made of any material manufactured in any manner which include the specified adapter features.

The adapter is shown in embodiments of FIGS. 1–11 that have one or two pockets. However, additional pockets may be used. In addition, each pocket was illustrated as having a single slit on each side. In some embodiments, two or more slits could be used. The slit may be aligned with the seam groove or the seam groove may not be aligned. Some adapters may not include slits, and instead simply have one of the following features: inner pocket support ribs, recesses to accommodate legs or other sample container protrusions, or handles and adapter compression features to aid in extraction of the adapter from a rotor device.

In some applications, it may be advantageous to enclose the sample container to prevent the escape of aerosol droplets or volatized compounds. The rotor bucket may include a cover for this purpose, such as the Aeroseal™ cover for buckets sold by Beckman Coulter (Fullerton, Calif.). Alternatively, the adapter may include a cover that encloses the tops of containers inserted into the adapter.

The present examples shown in FIGS. 1–11 illustrate embodiments of the present invention that include one or more slits dividing sections of the adapter. The inventors also envision two part adapters as an alternative means for allowing simplified extraction of the sample container from the adapter. The adapter sections could then be fit to receive one or more sample containers. Features on the adapter, such as pins and holes, or a tongue and groove system could allow the sections of the adapter to fit together. Such an adapter would retain the adapter structure such as structure to accommodate raised features on the exterior surface of the sample container, structure to support the walls of the sample container, indicia to indicate the proper insertion direction of the container and/or adapter structure to allow simplified extraction of the container from a recess into which the container is inserted. Such features could also be part of an adapter that does not have a slit, and instead simply has one or more pockets to hold a sample container. If the sample container does not have any raised features on the sides of the container, an adapter without a slit could be used while still allowing for maintenance of the integrity of the sample separation.

In the embodiments shown in FIGS. 1–10, the slit present was illustrated as on the sides of the adapter, with the hinge on the bottom. However, a hinge on one side of the adapter, with a slit on one side and on the bottom of the adapter is also envisioned as an embodiment of the present invention.

Figure 13:
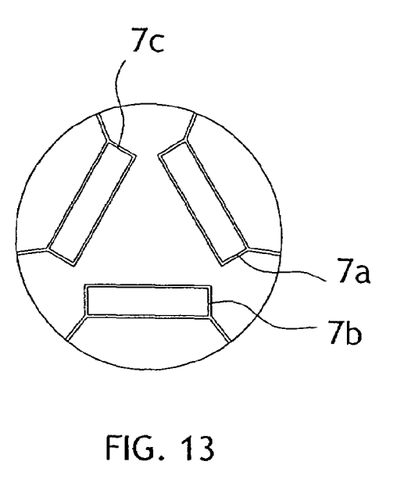
FIG. 13 is a top view of an alternate embodiment of the adapter.

In the embodiments shown in FIGS. 1–12, multiple sample containers are shown in parallel orientation. This has the advantage of subjecting the sample containers to similar hydraulic forces during a sample separation. Alternative sample container configurations are possible. For example, FIG. 13 illustrates a top view of an alternative layout for samples containers in an adapter. In this embodiment, each sample container pocket may include two slits, extending from corners of the pocket to the exterior walls of the adapter. Such slits would run from the top of the adapter to a mid-point in the bottom of the pocket to allow each pocket to divide into two sections, allowing efficient extraction of the sample container. Alternatively, as described above, the pockets could be constructed without slits.

The present invention should be adaptable to either fixed angle or "swinging" type rotors. In addition, the adapter could form a part of the rotor held device, with the rotor opening at a mechanical hinge to allow insertion of a sample container.

The features of the stated embodiments may be combined in various manners and still be within the inventors' understanding of the present invention.

What is claimed is:

1. A method of centrifuge separation in a flask of a type made of portions having external raised seam regions joining the portions together, said flask including a top end having an opening, a plurality of elongate walls including at least two rigid plastic parallel side walls, and a bottom opposite said top end, the method comprising:
   introducing a liquid into the flask;
   subjecting the flask to centrifugal forces by rotation in a centrifuge such that particulate matter migrates to the bottom of the flask; and
   supporting said flask in an adapter during said rotation, said adapter supporting the flask such that the flask maintains structural integrity during rotation by supporting flask walls during rotation.

2. The method of claim 1, wherein subjecting the flask to centrifugal forces by rotation in a centrifuge includes subjecting the flask to a force of between 100 and 2000 relative centrifugal force.

3. The method of claim 1, wherein said step of supporting the flask includes placing the flask into an adapter prior to said centrifuge rotation, said adapter supporting at least two parallel side walls of said flask within recessed areas in the adapter to accommodate projections from walls on said flask associated with the seam regions.

4. The method of claim 3, wherein said adapter is configured to hold more than one flask.

5. The method of claim 1, wherein said flask has a shorter cross sectional dimension and a longer cross sectional dimension and said step of rotating said flask includes orientating said flask during said rotation such that the longer cross sectional dimension is substantially oriented along the radius to a center of rotation when said flask is at rest, wherein rotation of the flasks alters this orientation by 90 degrees.

6. A method of centrifuge separation in a flask of the type made of portions having external seam regions joining the portions together, said flask including a top end having an opening, a plurality of elongate walls including at least two parallel, rigid plastic side walls, and a bottom opposite said top end, the method comprising:

introducing the flask containing a liquid into an adapter, said adapter supporting flask structure during a centrifuge separation such that said flask maintains structural integrity during centrifuge rotation by preventing force concentration at said external seam regions;

subjecting the adapter to centrifugal forces by rotation in a centrifuge such that particulate matter migrates to the bottom of the flask; and removing the flask from the adapter following rotation in the centrifuge.

7. The method of claim 6, wherein subjecting the adapter to centrifugal forces by rotation in a centrifuge includes subjecting the adapter to a force of between 100 and 2000 relative centrifugal force.

8. The method of claim 6, wherein said adapter is configured to hold more than one flask.

9. The method of claim 6, wherein said flask has a shorter cross sectional dimension and a longer cross sectional dimension and said step of rotating said flask includes orientating said flask for rotation such that the longer cross sectional dimension is substantially oriented along the radius to a center of rotation when said flask is at rest, wherein rotation of the flask alters flask orientation by 90 degrees.

10. The method of claim 6, further including a step of removing said flask from said adapter after rotation.

11. The method of claim 10, wherein said adapter includes a means for reducing disturbance of cells at a bottom of said flask.

12. The method of claim 10, wherein said adapter includes a means for reducing friction between said adapter and a device holding said adapter mountable on a centrifuge rotor.

* * * * *